(12) United States Patent
Lu et al.

(10) Patent No.: US 6,204,253 B1
(45) Date of Patent: Mar. 20, 2001

(54) FACTORS WHICH INTERACT WITH ONCOPROTEINS

(75) Inventors: Xin Lu; Shan Zhong, both of London (GB)

(73) Assignee: Ludwig Institute for Cancer Research, Zurich (CH)

( * ) Notice: Subject to any disclaimer, the term of this patent is extended or adjusted under 35 U.S.C. 154(b) by 0 days.

(21) Appl. No.: 09/269,617

(22) PCT Filed: Aug. 29, 1997

(86) PCT No.: PCT/GB97/02318

§ 371 Date: May 19, 1999

§ 102(e) Date: May 19, 1999

(87) PCT Pub. No.: WO98/13064

PCT Pub. Date: Apr. 2, 1998

(30) Foreign Application Priority Data

Sep. 26, 1996 (GB) .................................................. 9620028

(51) Int. Cl.⁷ .......................... C07H 21/04; C07H 21/02; C12Q 1/68; A01N 43/04; A61K 31/70
(52) U.S. Cl. .......................... 514/44; 435/69.1; 435/91.1; 435/325; 435/375; 435/6; 514/44; 536/23.1
(58) Field of Search .................................. 514/44; 435/6, 435/325, 91.1, 375; 536/23.1, 24.3, 24.5

(56) References Cited

U.S. PATENT DOCUMENTS 5,420,263  5/1995  Burrell et al. .................. 536/23.1

FOREIGN PATENT DOCUMENTS

| 0 781 844 | 7/1997 | (EP) . |
| 990082 | 4/1965 | (GB) . |
| WO 95/26973 | 10/1995 | (WO) . |
| WO 96/02642 | 2/1996 | (WO) . |
| WO 96/23225 | 8/1996 | (WO) . |
| WO 97/09343 | 3/1997 | (WO) . |

OTHER PUBLICATIONS

Andrea D. Branch, A good antisense molecule is hard to find, TIBS, 47–48, Feb. 1998.*

Trisha Gura, Antisense Has Growing Pains, Science, pp. 575–577, Oct. 1995.*

Stanley Crooke, Antisense Research and Applications, Chapter 1, Basic Principles of Antisense Therapeutics, Springer–Verlag Press, Berlin, Heidelberg, New York, p. 3, Jul. 1998.*

Shen et al., 1995, Proc. Natl. Acad. Sci. USA, 92:6778–82.

Su et al., 1996, Molecular Carcinogenesis 15:270–5.

Weeda et al., 1990, Cell, 62:777–91.

* cited by examiner

*Primary Examiner*—Robert A. Schwartzman
*Assistant Examiner*—Janet Epps
(74) *Attorney, Agent, or Firm*—Klauber & Jackson

(57) ABSTRACT

The invention relates to polypeptides that bind to the oncogene product mdm2 and the uses of the identified polypeptides in therapeutic compositions to treat aberrant cell division in humans.

6 Claims, No Drawings

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
       (A) LENGTH: 217 base pairs
       (B) TYPE: nucleic acid (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens
        (G) CELL TYPE: B-lymphocyte (vii) IMMEDIATE SOURCE:
        (A) LIBRARY: Human cDNA library
        (B) CLONE: SZ7

(xi) SEQUENCE DESCRIPTION: SEQ ID NO: 1:

```
GCCACGAAGG CCAACTCGTC CAACTGACAA GCCCTTNCNC CTGCCTCTCC AGGATGTCTA      60

CAAAATTGGT GGTATTGGTA CTGTTCCTGT TGGCCGAGTG GAGACTGGTG TTCTCAAACC     120

CGGTATGGTG GTCACTTTGC TCCAGTCAAC GTTACAACGG AAGTAAAATC TGTCGAATGA     180

CATGAGCTTT GAGTGAAGCT CTTCCTGGGA CATGTGG                              217
```

(2) INFORMATION FOR SEQ ID NO: 2:

(i) SEQUENCE CHARACTERISTICS:
        (A) LENGTH: 472 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens
        (G) CELL TYPE: B-lymphocyte (vii) IMMEDIATE SOURCE:
        (A) LIBRARY: Human cDNA library
        (B) CLONE: SZ10

(xi) SEQUENCE DESCRIPTION: SEQ ID NO: 2:

```
CCGCTCCCGA AGCTGANCAG GGCGGGGCTG ANTNAATGCC GGCTTACCAT CTCTACCATC      60

ATCCGGTTTA GTCATCCAAC AAGAAGAAAT ATGAAATTCC NGCCNTNNGA AATGAACNAA     120

AGATTGGAGC TGAAGACCTA AANTGCTTGC TTTTTTGGCC CGTTTGACCC NATTAATTTG     180

AACTTTCTGC CTTTATCTNN TTCCNCCNTG GGGGTTTTTT TTTATTTTTT TACCCTAAAA     240

NAACTTTCTC CTTTTTTGGG TTAATTAAAC CAAAACCTTT TTTTTTTTTT AANAAAAAAA     300

CCCCTGGGTT TTTTTTCCTC CAATTTAACC NCCCCTTTTT AAAANGGGTT TTTTTTTAAA     360

AATTTGGNTT TTCCCATTAN TCCTGGGGTT CCCCANTTTT TGNAAAAAAT TTTTTTTNAA     420

AGAAAAACTT TTCCNNTTTT TTTTTNAAAT TTTTTGGNTT NNATTNAAAA AN             472
```

(2) INFORMATION FOR SEQ ID NO: 3:

(i) SEQUENCE CHARACTERISTICS:
        (A) LENGTH: 198 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Homo sapiens
            (G) CELL TYPE: B-lymphocyte (vii) IMMEDIATE SOURCE:
            (A) LIBRARY: Human cDNA library
            (B) CLONE: SZ15

(xi) SEQUENCE DESCRIPTION: SEQ ID NO: 3:

GCCACGAAGG CATGTTGAGA AAGGCAAGAA GATTTTTATT ATGAAGTGTT CCCAGTGCCA      60

CACCGTTCAA AAGGGAGGCA AGCACAAGAC TGGGCCAAAT CTCCATGGTC TCTTTGGGCG     120

GAAGACAGGT CAGGCCCCTG GATTACTCTT ACACAGCNNC AATAAGAACA AAGGCATCAT     180

CTGGGAGAGG ATACACTG                                                   198

(2) INFORMATION FOR SEQ ID NO: 4:

(i) SEQUENCE CHARACTERISTICS:
            (A) LENGTH: 182 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Homo sapiens
            (G) CELL TYPE: B-lymphocyte (vii) IMMEDIATE SOURCE:
            (A) LIBRARY: Human cDNA library
            (B) CLONE: SZ16

(xi) SEQUENCE DESCRIPTION: SEQ ID NO: 4:

GCCACTAAGG CGCCACGAAG GCTCAGACCG AGACCGGCTC CGTTCGGAGA CAGAGAAAGA      60

GCTGGACCCA GATGGGCTGA AGAAGGAGTC AGAGCGGGAT CGGGCAATGC TGGCTCTCAC     120

ATTCCACTCT CAACAAACTC ATCAAAAGAC TGGAGGAAAA AGAGAGTCAG ATGCTGGTGA     180

AG                                                                    182

(2) INFORMATION FOR SEQ ID NO: 5:

(i) SEQUENCE CHARACTERISTICS:
            (A) LENGTH: 201 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Homo sapiens
            (G) CELL TYPE: B-lymphocyte (vii) IMMEDIATE SOURCE:
            (A) LIBRARY: Human cDNA library
            (B) CLONE: SZ17

(xi) SEQUENCE DESCRIPTION: SEQ ID NO: 5:

```
GCCACGAAGG CGTGAACGAA GCGGTGGGGA GCAGGCACAG GACTGGGATG CTCTGCCACC        60

CAAGCNGCCC CGACTACGAG GGAAACAAGA TCGGAGNCCG TACNTATTGT GGTGCTGGAA       120

GGGTCCAGTC TGGAGACAGT CAAGGTAGGG AAGACATATG CTACTCAACT GTGACAGCAC       180

AAGTCTATAT TGTTGAAGAA T                                                 201
```

(2) INFORMATION FOR SEQ ID NO: 6:

(i) SEQUENCE CHARACTERISTICS:
        (A) LENGTH: 216 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens
        (G) CELL TYPE: B-lymphocyte (vii) IMMEDIATE SOURCE:
        (A) LIBRARY: Human cDNA library
        (B) CLONE: SZ18

(xi) SEQUENCE DESCRIPTION: SEQ ID NO: 6:

```
GCCACGAAGG CCGCTCGTCA CCAGGACCCA AGGAACCAAA ATTGCATCTG ATGGTCTCAA        60

GGGTCGTGTG TTTGAAGTGA GTCTTGCTGA TTTGCAGAAT GATGAAGTTG CATTTAGAAA       120

ATTCAAGCTG ATTACTGAAG ATGTTCAGGG TAAAANCTGC CTGACTAACT TCCATGGCAT       180

GGATCTACCC GTGACAAATG TGTTCCATGG CTAAAA                                 216
```

(2) INFORMATION FOR SEQ ID NO: 7:

(i) SEQUENCE CHARACTERISTICS:
        (A) LENGTH: 167 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens
        (G) CELL TYPE: B-lymphocyte (vii) IMMEDIATE SOURCE:
        (A) LIBRARY: Human cDNA library
        (B) CLONE: SZ27

(xi) SEQUENCE DESCRIPTION: SEQ ID NO: 7:

```
GCCACGAAGG CGTAAAACCG ACCCCATGAC CCCTAACAGG GCCCTCTCAG CCCTCCTAAT        60

GACCTCCGGC CTAGCCATGT GATTTCACTT NCACTCCATA ACGCTCCTCA TACTAGGCTA       120

CTAACCAACA CACTAACCAT ATACCAATGA TGGCCGCATG TAACACG                     167
```

(2) INFORMATION FOR SEQ ID NO: 8:

(i) SEQUENCE CHARACTERISTICS:
        (A) LENGTH: 211 base pairs
        (B) TYPE: nucleic acid

```
            (C) STRANDEDNESS: single
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Homo sapiens
            (G) CELL TYPE: B-lymphocyte (vii) IMMEDIATE SOURCE:
            (A) LIBRARY: Human cDNA library
            (B) CLONE: SZ38

(xi) SEQUENCE DESCRIPTION: SEQ ID NO: 8:

GCCACGAAGG CCCGCAACCC TGTCCTTGTC AGAGGAATTG GCAGGTATTC CCGATCTGCC        60

ATGTATCCAG AAAGGCCATG TACAAGAGGA AGTACTCAGC CGCTAAATCC AAGGTGAAAA       120

GAAAAAGAAG GAGAAGGTTC TCGCAACTGT TACAAAACCA GTTGGTGGTG ACAAGAACTG       180

GCACTGGATC CCGTGTGGTT AACTTCGCAA A                                     211

(2) INFORMATION FOR SEQ ID NO: 9:

(i) SEQUENCE CHARACTERISTICS:
            (A) LENGTH: 172 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Homo sapiens
            (G) CELL TYPE: B-lymphocyte (vii) IMMEDIATE SOURCE:
            (A) LIBRARY: Human cDNA library
            (B) CLONE: SZ12

(xi) SEQUENCE DESCRIPTION: SEQ ID NO: 9:

GCCACGAAGG CAGAAAATCC AAGTCCGGCT AGTACGCGAA TTGGAGAAAA AGTTCAGTGG        60

GAAGCATGTC GTCTTTATCG CTCAGAGGAG AATTCTGCCT AAGCCAACTC GAAAAAGCCG       120

TACAAAAAAT AAGCAAAAGC GTCCAGGAGC CGTACCTGAC AGCTGTGCAC GA              172

(2) INFORMATION FOR SEQ ID NO: 10:

(i) SEQUENCE CHARACTERISTICS:
            (A) LENGTH: 219 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Homo sapiens
            (G) CELL TYPE: B-lymphocyte (vii) IMMEDIATE SOURCE:
            (A) LIBRARY: Human cDNA library
```

(B) CLONE: SZ34

(xi) SEQUENCE DESCRIPTION: SEQ ID NO: 10:

GCCACGAAGG CAGGAATATG CCATTCGACT GAACAAACCC TATATCTACG GACCTACGTG      60

TCAGGGGAA AGGATGCAAA TTCTCCAGAA TTTCAAGCAC AACCCCAAAA TTAACACCAT      120

CTTCATATCC AAGGTAGGTG ACACTTCGTT TGATCTGCCG GAAGCAAATT GTCTCATTCA      180

GATCTCATCC CATGGTGGCT CCAGGCGTCA GGAAGCCAA                            219

(2) INFORMATION FOR SEQ ID NO: 11:

(i) SEQUENCE CHARACTERISTICS:
        (A) LENGTH: 1039 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens
        (G) CELL TYPE: B-lymphocyte (vii) IMMEDIATE SOURCE:
        (A) LIBRARY: Human cDNA library
        (B) CLONE: SZ29

(xi) SEQUENCE DESCRIPTION: SEQ ID NO: 11:

CACTACAATG GATGATGTAT ATAACTATCT ATTCGATGAT GAAAGATACC CCACCAAACC      60

CAAAAAAGA GATCTGGAAT TCGGATCCTC GAGGCCACGA AGGCCGGAAA TCTGAAGCAA      120

AGAAGGAATC ACTTCCCAGA AGAAGAAGCC TGCATATCGA ACCTTTATTA AAGGAAAAAA      180

TTACATGAAG CAACGGGATG ACATTTTGAT TAACAGGCCN GCAAAGAANC ACCTANAATT      240

GTATGACAGG GATCTGAAAC ATTTTCGGAT CTCTAAGGCN CTCGATANAN TTCTTGATCC      300

CACTTGTNCA ATAAAGACAC CCGAGATTNC GGTGTCCATC ATAAAGGAGT TNAATCGAAG      360

AAGAGTCCTT GCAAATGCGC TTGCANGTCT GGATGAAAAA GAAATCANTC NTGTTCTTAA      420

TTTTTTGATA ANGAATCTNT CTCCCCNAGA TTTGCCCCTG TTTTAATCNN TGCTGCTGAA      480

ATAATTATTG ATATATATCT GCCTGTNATT GGTCCTCCCC TGTANTTGAT AAAAAGTTTT      540

TACTACTTCN NGGACTTGTT TAAAAAGANA TTGATTNCCC AGANAATTGT TNAAACCTTG      600

GGGGATGATN GATATGCTNT TGCCCCNTGA AAAAGAAGGA AGGCCNTCTT TNTTTGNACA      660

CCCCTCTGAT GGATTCCCCA AAATAANAAA ATAAATCCTN NTGTCTGCTA ATAAAACTNT      720

AAAACTCCNA AATTTGAATA AATTTGACTG TTTTNATTTT TGGGAAAAAA NCNCTTTGAT      780

ACTTTTAAAA ACTGTTTGCN AAACCCTTCT NTGGAAAAAA CGGAATAATT TTGGCCGGAA      840

ACCATTTCCC TTTTAANTTT AAAATGGTTT CCCCTTTTNT TTTGAATTTT ACCCCTCCCC      900

NNAAAATTTC CNTTTTTTTT CCCCAATTTG TTTTCNTGGG ATGGAATTTA NTTTTATACC      960

GGATTTTTTT TTTCCCCNTT TGGTTTGTTT TCCATTGGGA ATCCATTTAA ACCCCCCNGG     1020

AAAAGGTCCC TNGGAACCN                                                 1039

(2) INFORMATION FOR SEQ ID NO: 12:

(i) SEQUENCE CHARACTERISTICS:
        (A) LENGTH: 155 base pairs
        (B) TYPE: nucleic acid (C) STRANDEDNESS: single
                (D) TOPOLOGY: linear (ii) MOLECULE TYPE: cDNA (iii) HYPOTHETICAL: NO (iv) ANTI-SENSE: NO (vi) ORIGINAL SOURCE:
                (A) ORGANISM: Homo sapiens
                (G) CELL TYPE: B-lymphocyte (vii) IMMEDIATE SOURCE:
                (A) LIBRARY: Human cDNA library
                (B) CLONE: SZ2

(xi) SEQUENCE DESCRIPTION: SEQ ID NO: 12:

GCCACGAAGG CGTTTCACGT CTTCGCCAAT CACAGTGCAG CAAGGCCAAT TCTCTCAGAA     60

ACCCCCACGT GTGCACAGTG GGAGAGGGGA AAGAGAAAAA AAGGTGAGCA TGGAGGAAAA    120

AGGTACTGGA TAAAGTAAAC TTCAAACCTT AGGGC                               155

(2) INFORMATION FOR SEQ ID NO: 13:

(i) SEQUENCE CHARACTERISTICS:
                (A) LENGTH: 1025 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (vi) ORIGINAL SOURCE:
                (A) ORGANISM: Homo sapiens
                (G) CELL TYPE: B-lymphocyte (vii) IMMEDIATE SOURCE:
                (A) LIBRARY: Human cDNA library
                (B) CLONE: SZ33

(xi) SEQUENCE DESCRIPTION: SEQ ID NO: 13:

GNNNNNNNNT TNCTCCNCTA CAATGGATGA TGTATATAAC TACCTATTCG ATGATGAAGA     60

TACCCACCAA ACCCAAAAAA AGAGATCTGG AATTCGGATC CTCGAGGCCA CGAANGCCGG    120

CCTTCGTGGC CGAAAAGAGC TGAGCGGAGA CCAAAGTCAG CCGGGAGACA GTGGGTCTGT    180

GAGAGACCGA ATAGAGGGGC TGGGGCCACG AGCGCCATTG ACAAGCAATG GGGAAGAAAC    240

AGAAAAACAA GAGCGAAGAC AGCACCAAGG ATGACATTGA TCTTGATGCC TTGGCTGCAG    300

AAATAGAANG AGCTGGTGCT GCCAAAGAAC AGGAGCCTCN AAAGTCNAAA GGGAANAAGA    360

ANAAAGAGAA NANNAAGCAG GACTTTGATG AAGATGATAT CCTGAAAGAA CTGGAAGAAT    420

TGTCTTTGGA AGCTCAAGGC ATCNAAGCTG ACAGANAAAC TGTTGCAGTG AAGCCNACAG    480

AAAACAATGA AGAAGAATTC CCCTCCNAGA TNNNNNNNAG AAAGGACCGA AGGGCNAAAA    540

ACAGAATTTT GATGATAATG ATACGAAGAA TTGGAAGATA AAGATTCCNA ATCCANAAAG    600

ACTGCNAAAC CGAAAGTGGA AATTTCTCTG GGANTGATGA TGATGATGAT TTTAACCAAC    660

TTCCTAAAAA ACTNAAGGGA AAGCTCCNAA ATCAATAANA AATTGGATGG TCCAAGAAGA    720

TGAGGATACC TTNNNAATTT ANGANCTTCA NAATAATTCT CTGGTGAAAT TGTGATAATC    780

CATAATTTTG CNTCTTNAAA NGGCGAAAAA NTCNAAAACC NCCCGTTCTN CCTTNAANTT    840

GGATGAAAAT ATACCCNCCT CCAATTAAAC NTGGCCCNAA NAAGGCAANN NAGGACNCAA    900

```
NAAAAAACCA AATAAAAAAA CNAACNCGGA ACTGAANAAA AAAAAATTTA AACCGTTTNG        960

GTTTAATTTC CNNGGTTNCC CGGGANTTNA AAAAAAANTT GCCTCCTGCC CCAAATTNTT       1020

AANCN                                                                  1025
```

(2) INFORMATION FOR SEQ ID NO: 14:

(i) SEQUENCE CHARACTERISTICS:
        (A) LENGTH: 1042 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens
        (G) CELL TYPE: B-lymphocyte (vii) IMMEDIATE SOURCE:
        (A) LIBRARY: Human cDNA library
        (B) CLONE: SZ37

(xi) SEQUENCE DESCRIPTION: SEQ ID NO: 14:

```
GNNNNGNNTT CNNCCACTAC AATGGGATGA TGTATATAAC TACCTATTCG ATGATGAAGA         60

TACCCACCAC ACCCNAAAAA AAGAANNTCT NGGATTCCGG NTCCTCGAGG CCACGAAAGG        120

CCGGCCTTCG TGGCCGAAAA GAGCTGAGCG GAGACCAAAG TCNGCCGGGA GACAGTGGGT        180

CTGTGAGAGA CCGAATAGAG GGGCTGGGGC CACGAGCGCC ATTGACAAGC AATGGGGAAG        240

AAACAGAAAA ACAAGAGCGA AGACAGCACC AAGGATGACA TTGATCTTGA TGCCTTGGCT        300

GCANAAATAG AAAGAGCTGG TGCTGCCNAA GAACAGGAGC CTCNNAAGTC TCNAGGGAAA        360

NAGAAAAANAG AGAATANNNA GCCCGACTTT GATGAAGATG ATATCCTGAA AGAACTGGAA       420

GAATTGTCTT TGGAACTCNN GGCATCTAAG CTGACAGANA AACTGTTGCN NTGAAGCCCC        480

CANAAAACNA TGAAGAAGAA TCCCCTCCCN AGATTNNNNA NAGAAAGGAC ANANGGGCCN        540

NAACAGANTT TTGATGATAA TGATAGCGAA NAATTGGAAG ATATAGATTC NCAATCNCNN        600

NAGACTGCCC ANCCNAAAGT GGAAATTTNT CTNGGAGTGA TGATGATGAT GATTTAACAN        660

ACTTCCTCNA AAANCTNNAG GGAAAGCTCC AAATCNNATA ANAAATNNGA TGGGTCTCAA        720

GAAGATNAGG ATACNTTTNN NATTTTNAAC GTCCCNAATA AATTCCTCTN GTGAAATTGT        780

GATAATCCAT AATTTTTGCC TCTCCAAAAG GACCAAAAAA ATCCAAAANC CNCCCCNTCC        840

CCCTTNAAAT TNGATTANAA TTTACCCNCC TCCCATTTAA ACCTGNCCCN NAAGGCGAAA        900

AAAAGGGCNC CNANNAAANN CCCANTAATA ANAACCNACC GCGGGGCTTA NNAAANAAAA        960

ATTTAACCGT TTTNGGTTNA TTTCCNCNGG ACCCCCNGGA TTTTAAAAAA CTTTGCCTCC       1020

TGGCCCCAAA TTTTTAATCT AA                                               1042
```

FACTORS WHICH INTERACT WITH ONCOPROTEINS

FIELD OF THE INVENTION

The invention relates to the oncoprotein mdm2 (murine double minutes), and more specifically, agents which interact therewith and which can thus influence cell growth regulation and which have use particularly, but not exclusively, as therapeutics, diagnostics, prognostics and in assays and as models designed to elucidate cell growth regulation.

BACKGROUND OF THE INVENTION

The oncoprotein mdm2 (murine double minutes) was originally isolated through its ability to transform mouse BALB/c fibroblast cells (Fakharzadeh, et al., 1991). In the transformed cells, the mdm2 gene is often amplified and exists as a double minute chromosome. The mdm2 gene encodes a protein of 491 amino acids and contains all the domains necessary for being a transcription factor. It has a consensus nuclear translocation signal, two zinc binding domains and acidic and basic domains (Brown, et al., 1993). The mdm2 gene is located on human chromosome 12q13-14 and is often seen to be co-amplified with the CDK4 gene (a cyclin dependent kinase gene which is located within the same region) in human malignant gliomas (He, et al., 1994, Reifenberger, et al., 1995). Amplification of the mdm2 gene has also been found in a variety of human sarcomas (Ollner, et al., 1992; Ladanyl, et al., 1993; Khatib, et al., 1993). Amplification of the mdm2 gene is, however, not universal; many tumours, including some types of leukaemia, were found to have no amplification of the mdm2 gene (Ridge, et al., 1994). Nevertheless, abnormal expression of the mdm2 gene has been found in many types of human tumour. Abnormal expression of mdm2 has been reported in chronic lymphocytic leukaemia (Watanbe, et al., 1994; Huang, et al., 1994). Elevated mdm2 expression was also found in Hodgkin's and non-Hodgkin's lymphomas at both mRNA and protein levels (Chllosl, et al., 1994, Finnegan, et al., 1994). High levels of expression of the mdm2 gene have been linked to a poor response to chemotherapy and short survival in haematological malignancies (Quesnel, et al., 1994).

SUMMARY OF THE INVENTION

The best known function of mdm2 is its ability to bind to the tumour suppressor protein p53 via its transcriptional activation domain (Lin, et al., 1994), thus inhibiting the p53 transcription activity (Momand et al., 1992). In addition, mdm2 has been shown to be able to block p53 induced apoptosis in some cell lines. A recent study also demonstrated that inactivation of the mdm2 gene can result in the embryonic lethality, a phenotype that could be rescued by a p53 null background. All these observations suggest that one of the important functions of mdm2 is its ability to block the activity of p53. However, recent reports showed that mdm2 can also bind to another tumour suppressor gene product Rb (Xiao, et al., 1995) as well as a cell cycle transcription factor E2F1 (Martin, et al., 1995). Interestingly, all three tumour suppressor proteins, p53, Rb and E2F1 (Field et al, 1996), are key players in controlling cell cycle progression and apoptosis, suggesting that mdm2 may play a key role in regulating cell growth. Although the mdm2 protein has many features characteristic of transcription factors and the phenomena listed above are well established, there is little understanding of the true biological function of mdm2. It is, however, clear that mdm2 occupies a key role in cell growth regulation.

A biological role for mdm2 is suggested by the following data. Using FACS analysis as described in Hseih et al 1997, cells selected containing a sub-G1 DNA content (typical of cells undergoing apoptosis) it has been shown that in the presence of Rb the anti-apoptotic function of mdm2 is abolished. It is known that mdm2 targets p53 for degradation, possibly via the ubiquitination pathway. In the presence of Rb, p53 is stabilised. Therefore interaction between Rb and mdm2 can promote the tumour suppressor activity of p53.

Mdm2 interacts with and is phosphorylated by cyclinA-cdk2 (a S-phase cyclin-cdk complex Lu unpublished data). It has been shown previously that cyclins are targets for ubiquitination. As p53 is also a target for ubiquitination it is possible that mdm2 interaction is causally related to degradation of these important cell-cycle proteins or indeed to the ubiquitination of mdm2. Saos-2 and HI299 cells (null for p53) treated with the proteosome inhibitor ALLN (a calpain proteinase inhibitor) results in an increase in the cellular levels of mdm2. This suggests that mdm2 is a target for ubiquitination in the absence of p53. It may therefore be possible to regulate the negative effects of mdm2 on p53 by alternative strategies.

It is therefore an object of the invention to identify agents which interact with mdm2 and thus have therapeutic, diagnostic or prognostic application.

It is yet a further object of the invention to identify agents which can influence cell growth and regulation via binding to mdm2.

It is yet a further object of the invention to elucidate the role of mdm2 in cell growth regulation by identifying agents that interact therewith with a view to then determining the nature of the pathway involved and thus agents which may be of potential use in regulating said pathway.

It is yet a further object of the invention to provide a methodology for identifying the aforementioned agents.

DETAILED DESCRIPTION OF THE INVENTION

It will be apparent that agents which interact with mdm2 i.e. those sequences identified in Tables 1 and 2 have potential as therapeutic agents in various processes relating to cell growth and division. A relatively recent alternative strategy to traditional therapies is the use of antisense molecules to regulate the production and/or availability of translatable mRNA to targeted nucleic acid sequences. Clearly some of the identified sequences show elevated expression in certain transformed cells and their down regulation has been linked to a reversion of the transformed phenotype.

As mentioned above, the invention embraces antisense oligonucleotides that selectively bind to a nucleic acid molecule presented in Tables 1 and 2, to decrease transcription and/or translation of these genes. This is desirable in virtually any medical condition wherein a reduction in gene product expression is desirable, including to reduce any aspect of a tumour cell phenotype attributable to the expression of that sequence. Antisense molecules, in this manner, can be used to slow -down or arrest such aspects of a tumour cell phenotype.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and thereby, inhibits the transcription of that gene and/or the translation of that mRNA. The antisense molecules are designed so as to interfere with transcription or translation of a target gene upon hybridization with the target gene. Those skilled in the art will recognise that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon the DNA sequence presented in Tables 1 and 2 or upon allelic or homologous genomic and/or DNA sequences, one of skill in the art can easily choose and synthesize any of a number of appropriate antisense molecules for use in accordance with the present invention. In order to be sufficiently selective and potent for inhibition, such antisense oligonucleotides should comprise at least 7 (Wagner et al., *Nature Biotechnology* 14:840–844, 1996) and more preferably, at least 15 consecutive bases which are complementary to the target. Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439–457. 1994) and at which proteins are not expected to bind. Finally, although Tables 1 and 2 discloses cDNA sequence, one of ordinary skill in the art may easily derive the genomic DNA corresponding to the cDNA of Tables 1 and 2. Thus, the present nvention also provides for antisense oligonucleotides which are complementary to the genomic DNA corresponding to Tables 1 and 2. Similarly, antisense to allelic or homologous DNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognised methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, phosphate triesters, acetamidates, peptides, and carboxymethyl esters.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-0-alkylated ribose group. In addition, modified oligonucleotides may include sugars such as arabinose instead of ribose. Modified oligonucleotides also can include base analogs such as C-5 propyne modified bases (Wagner et al., *Nature Biotechnology* 14:840–844, 1996). The present invention, thus, contemplates pharmaceutical preparations containing modified antisense molecules that are complementary to and hybridizable with, under physiological conditions, nucleic acids presented in Tables 1 and 2, together with pharmaceutically acceptable carriers.

Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

According to a first aspect of the invention there is therefore provided the use of at least one agent as identified in Table 1 or 2, or a homologue or analogue thereof, or a functionally effective fragment thereof, for binding with mdm2 and thus influencing cell growth regulation.

It will be apparent that the term agent can refer to any small molecule or ligand (e.g. antibody) that can bind to mdm2 and thus interfere with mdm2 function. Since, it is known that interactions of mdm2 with the tumour suppressor proteins p53 and Rb imply mdm2 prevents tumour suppressor function it therefore follows that those agents that interfere with the interaction between mdm2 and p53 or Rb will release p53 or Rb from mdm2 and so stop cell growth. These agents therefore can significantly influence the functioning of mdm2 and moreover will have use as therapeutics.

According to a further aspect of the invention there is provided a therapeutic composition comprising at least one agent as identified in Table 1 or 2, or a homologue or analogue thereof, or a functionally effective fragment thereof, and a suitable excipient or carrier.

According to a yet further aspect of the invention there is provided a diagnostic or prognostic assay for predicting or determining cell growth regulation which assay comprises identifying the existence of, or cellular levels of, any one or more of the agents identified in Table 1 or 2, or a functionally effective fragment thereof, with a view to determining the likelihood of, or existence of, mdm2 binding to said agent or said fragment.

It will therefore be apparent that given that mdm2 interacts with the agents identified in Table 1 or 2 then the degree of interaction will have an effect on cell growth regulation given the role that mdm2 has to play in cell growth regulation. Therefore, an assay to determine the nature of this interaction will have use in determining aspects of cell growth regulation.

In a preferred embodiment of the invention the assay may be a competitive binding assay of a conventional nature such as a radio-immunoassay or an immunoassay. Assays of his nature are well known to those skilled in the art and so need not be described herein in detail.

According to a further aspect of the invention there is provided a methodology for identifying agents that interact with mdm2 which methodology employs a yeast two hybrid assay as herein described.

Notably, insofar as the agents identified in Table 1 or 2 are concerned OS-9 is amplified in human sarcomas and furthermore over expression of S3 and C140 is found in human colon rectal and thyroid tumours respectively. This tends to imply that not only do these agents have a role to play in influencing the functioning of mdm2, as aforedescribed, but conversely, mdm2 may have a role to play in effecting the function of a OS9, S3 and C140. Thus, it follows, that in some instances mdm2 may have a role to play as a therapeutic agent in treating at least human sarcomas, human colon rectal tumours and human thyroid tumours.

Moreover, it is also important to note that mdm2 interacts with human DNA binding protein (Enhancer Factor 1) which can bind to erb-B-2 and EGFR. It therefore follows that mdm2 may control erb-B-2 expression in human breast tumours and thus, again, agents which can interfere with the activity of mdm2 may be used to prevent its binding with human DNA binding protein and so prevent expression of erb-B-2.

Further evidence for the involvement of mdm2 in breast cancer is given by the following data. If an mdm2 expression plasmid and a reporter plasmid containing the multi-drug resistance gene mdr1 are co-transfected into human breast carcinoma cell line MCF-7, a 50–200 fold inhibition of transcriptional activity of the mdr1 gene is detected. The mdr1 gene is regulated at the level of transcription and the promoter of mdr1 has been shown to bind the transcription factor YB-1, a protein herein described as a target for mdm2.

Further, it is known that mdm2 interacts with L6/TAXREB107 which in turn binds to Tax responsive element in the LTR region of HTLV-1. It therefore follows that mdm2 can effect the function of TAX and the activity of HTLV-1. It is also possible that it may effect the activity of HIV since there are sequence similarities between HTLV-1 and HIV. It therefore follows that agents that bind with mdm2 may prevent the interaction of same with L6/TAXREB 107 and so may be used to alleviate or treat symptoms associated with expression of HTLV-1 or HIV genes.

Further, mdm2 interacts with S3, S7, L6, EF1α and YB-1. Since these are all important proteins involved in protein translation it follows that mdm2 has a key role to play in controlling protein synthesis. Accordingly, any one or more of the agents listed in Table 1 or 2, other than S3, S7, L6, EF1a and YB-1 may be used to inhibit protein synthesis.

In addition, mdm2 interacts with ERCC3/XP-B which is a key component in nucleotide excision repair, for example, to repair UV damaged DNA. Indeed, the human homologue of ERCC3 ie XP-B is the gene lacking in the Group B Patients suffering from cancer prone syndrome xeroderm pigmentosom. ERCC3XP-B is also a component of transcriptional factor TFIIH. ERCC3/XP-B is also implicated in p53 induced apoptosis and this may be mediated by its ability to interact with p53. The ability of mdm2 to interact with ERCC3/XP-B may represent another means by which mdm2 can influence p53 expression and thereby control DNA repair and apoptosis. It therefore follows that ERCC3/XP-B is important in gene expression. Accordingly, any one or more of the agents listed in Table 1 or 2, other than ERCC3/XP-B, may be used to interfere with gene expression.

According to a further aspect of the invention there is provided use of an agent identified in Table 1 or 2, other than S3, L6 or EF1a, or a homologue or analogue thereof, or functionally effective fragment thereof, to inhibit protein synthesis.

Further, it is of note that S3 also comprises AP endonuclease activity as well as endonuclease III activity. Therefore mdm2 would seem to have a role to play in DNA repair and accordingly agents other than S3 or AP listed in Table 1 or 2 may be used to inhibit said repair and so affect damaged DNA processing.

According to a yet farther aspect of the invention there is provided use of an agent identified in Table 1 or 2, other than S3 or AP, or a homologue or analogue thereof, or functionally effective fragment thereof—to inhibit DNA repair.

Further, since mdm2 has oncogenic activity its activity may be modulated by its interaction with any one or more of the proteins listed in Table 1 or 2.

Embodiments of the invention will now be described, by way of example only, with reference to the following methodology and Table 1 and 2 wherein;

Table 1 is a list of known agents which have been shown to bind to mdm2 using the methodology hereinafter described and Table 2 represents the corresponding DNA sequence structure of the agents listed in Table 1 and also the DNA sequence structure of other agents whose sequence structure has been elucidated but whose characterisation is unknown.

EXAMPLE 1

Isolation of Novel mdm2 Interacting Proteins

The yeast two hybrid assay is based on the fact that many eukaryotic transcriptional activators (GAL4 for example) consist of two physically separable modular domains, such as DNA binding and transactivation domains. When two separated domains such as DNA binding and transcriptional activation domains are brought together through protein-protein interactions, they can function as a transcription activator and turn on the relevant reporter genes. Yeast strain HF7c contains two different GAL4 reporter genes HIS3 and LacZ under the control of dissimilar promoters. Using this yeast two hybrid system, Human mdm2 cDNA was cloned into a yeast expression vector pGBT9 to produce a GAL4 binding domain containing mdm2 fusion protein. The pGBT9-mdm2 plasmid was then transformed into yeast strain (HF7c). pGBT9-mdm2 alone is not sufficient to turn on the reporter gene in yeast HF7c. pGBT9-mdm2 transformed yeast colonies were expanded and their mdm2 expression was detected by anti-mdm2 antibody SMP14.

Clones expressing mdm2 at high level were grown into large quantities and used to carry out the library screening. A human B cell cDNA library (Gift from Dr. Steve Elledge) cloned into yeast expression vector pACT, which contains the transcriptional activation domain of GAL4, was subsequently transformed into pGBT9-mdm2 containing HF7c strain. The library screening and selection procedure were mainly based on the manual from Clontech (matchmaker™ two hybrid system). If mdm2 interacts with a protein derived from the yeast expression library, such interaction will bring together the GAL4 DNA binding domain (in pGBT9mem2) and transactivation domain (from pACT vector which was used to construct the library). Such interaction will then transactivate the expression of HIS3 and LacZ genes. The expression of HIS3 will allow the yeast to grow in the medium lacking the amino acid histidine. Transactivation of LacZ gene will turn on the β-galactosidase activity and this can make the transformed yeast colonies turn blue in a β-galactosidase assay.

The transformed yeast were selected for their ability to grow in the medium lacking the amino acid Histidine. The resistant colonies were then tested for their β-galactosidase activity. The colonies which turned blue within 2 hours in the β-galactosidase assay were isolated and cultures on 3-AT(3-aminotriazole) containing plate in order to select the strong interacting proteins. The resistant colonies were cultured and the DNA from these colonies were isolated. The DNAs were analysed by PCR to identify the known interacting proteins such as p53 and Rb. The DNAs other than p53 and Rb were then transformed into *E. Coli* HB101 under Leu selection to eliminate the pGBT9 plasmid. The DNA from HB101 was then subsequently transformed into *E. Coli* DH5a. DNAs from these DH5a colonies were then isolated and re-transformed into yeast strain HF7c with either pGBT9-mdm2 (positive control) or pLAM5[1] (negative control). The DNAs which can result in the yeast growth in the absence of amino acid histidine and turn on the β-galactosidase activity when co-transformed with pGBT9-mdm2 but not pLAM5[1] were considered as true positives. In total, 26 positive clones were identified and among them 4 contain the same sequence.

EXAMPLE 2

Implications of mdm2 Function through its Interaction with the Identified Proteins Using the sequence from the identified clones to search the gene data base, it was clear that the sequences derived from four of the clones were encoding for four different unknown proteins as summarised in Table 1 or 2. Among the characterised sequences, the sequence identity to known genes is summarised in Table 1.

It can therefore be seen that we provide an assay for identifying agents that bind to mdm2 and so have a role to play in many aspects of cell processing.

TABLE 1

| Yeast clones | names of the known genes and functions |
|---|---|
| SZ7 | Elongation factor 1a protein translation |
| SZ10 | Human DNA binding protein |
| | (1) DNA binding protein, transcription enhancer |
| | (2) Binds to the promoters of erb-B-2 and EGFR |
| SZ15 | Cytochrome C |
| SZ16 | OS-9 |
| | (1) ubiquitously expressed |
| | (2) amplified in human sarcomas |
| SZ17 | Sequence from yeast two hybrid assay |
| SZ18 | Ribosomal protein S3/v-fos transformation effector Fte-1 |
| | (1) Component of ribosomal small subunit, binds to 18S RNA. |
| | (2) Recombinant S3 and purified S3 from mouse cells contain AP1 endonuclease activity as well as endonuclease III activity which are important in DNA repair. |
| | (3) Overexpression in Fanconi's anemia cell lines will cause resistance to DNA cross linking agents such as mitoycinC and dlepoxybutane. |
| | (4) *E. coli* S3 is a DNA binding protein. |
| | (5) S3 locates in nucleus and cytoplasm |
| | (6) Fte-1 is overexpressed 4–5 fold in v-fos transformed cells. |
| | Fte-1 level reduced to normal level in v-fos revertant cells. |
| | (7) Overexpressed in human colon cancers and polyps. |
| SZ27 | cytochrome oxidase I.II |
| SZ38 | Ribosomal protein L6/TAXREB107. C140 |
| | (1) L6 is a component of ribosomal large subunit and it can bind to 5sRNA. |
| | (2) TAXREB107 is a DNA binding protein and it binds to HTLV-1 tax responsive element. |
| | (3) L6/TAXREB107 has very high sequence homology to C140. C140 is markedly increased in malignant transformed thyroid tumour cells, 5.8 fold higher than the normal. |
| SZ12 | Ribosomal protein S7 |
| SZ34 | ERCC3/XP-B |
| | (1) Human homolog of ERCC3 is XP-B, which is the gene lacking in the group B patients suffering from cancer prone xeroderma pigmentosom. |
| | (2) ERCC3/XP-B is a key component in nucleotide excision repair (to repair UV damaged DNA). |
| | (3) ERCC3/XP-B is also a component of transcription factor TFIIH, therefore it involves in general transcription. |

TABLE 2

SZ7/elongation factor 1a (SEQ ID NO:1)
GCCACGAAGGCCAACTCGTCCAACTGACAAGCCCTTNCNCCTGCCTCTCCA

GGATGTCTACAAAATTGGTGGTATTGGTACTGTTCCTGTTGGCCGAGTGG

AGACTGGTGTTCTCAAACCCGGTATGGTGGTCACTTTGCTCCAGTCAACGT

TACAACGGAAGTAAAATCTGTCGAATGACATGAGCTGAGTGAAGCTCTTCCTG

GGACATGTGG

TABLE 2-continued

SZ10/dbp (SEQ ID NO:2)
CCGCTCCCGAAGCTGANCAGGGCGGGGCTGANTNAATGCCGGCTTACCATCTCTA

CCATCATCCGGTTTAGTCATCCAACAAGAAGAAATATGAAATTCCNGCCNTNNGA

AATGAACNAAAGATTGGAGCTGAAGACCTAAANTGCTTGCTTTTTTGGCCCGTTT

GACCCNATTAATTTGAACTTTCTGCCTTTATCTNNTTCCNCCNTGGGGGTTTTTTT

TATTTTTTTACCCTAAAANAACTTTCTCCTTTTTTGGGTTAATTAAACCAAAACCTT

TTTTTTTTTTTAANAAAAAAAACCCCTGGGTTTTTTTTCCTCCAATTTAACCNCCCCT

TTTTAAAANGGGTTTTTTTTTAAAAATTTGGNTTTTCCCATTANTCCTGGGGTTCC

CCANTTTTTGNAAAAAATTTTTTTTNAAAGAAAAACTTTTCCNNTTTTTTTTTNAA

ATTTTTTGGNTTNNATTNAAAAAN

SZ15/cytochrome C (SEQ ID NO:3)
GCCACGAAGGCATGTTGAGAAAGGCAAGAAGATTTTTATTATGAAGTGTTCCCAG

TGCCACACCGTTCAAAAGGGAGGCAAGCACAAGACTGGGCCAAATCTCCATGGT

CTCTTTGGGCGGAAGACAGGTCAGGCCCCTGGATTACTCTTACACAGCNNCAATA

AGAACAAAGGCATCATCTGGGAGAGGATACACTG

SZ16/OS-9 (SEQ ID NO:4)
GCCACTAAGGCGCCACGAAGGCTCAGACCGAGACCGGCTCCGTTCGGAGACAGA

GAAAGAGCTGGACCCAGATGGGCTGAAGAAGGAGTCAGAGCGGGATCGGGCAA

TGCTGGTCTCACATTCCACTCTAACAAACTCATCAAAAGACTGGAGGAAAAAG

AGAGTCAGATGCTGGTGAAG

SZ17/Hela sequence (SEQ ID NO:5)
GCCACGAAGGCGTGAACGAAGCGGTGGGGAGCAGGCACAGGACTGGGATGCTCT

GCCACCCAAGCNGCCCCGACTACGAGGGAAACAAGATCGGAGNCCGTACNTATT

GTGGTGCTGGAAGGGTCCAGTCTGGAGACAGTCAAGGTAGGGAAGACATATGCT

ACTCAACTGTGACAGCACAAGTCTATATTGTTGAAGAAT

SZ18/S3/Fte-1 (SEQ ID NO:6)
GCCACGAAGGCCGCTCGTCACCAGGACCCAAGGAACCAAAATTGCATCTGATGG

TCTCAAGGGTCGTGTGTTTGAAGTGAGTCTTGCTGATTTGCAGAATGATGAAGTT

GCATTTAGAAAATTCAAGCTGATTACTGAAGATGTTCAGGGTAAAANCTGCCTGA

CTAACTTCCATGGCATGGATCTACCCGTGACAAATGTGTTCCATGGCTAAAA

SZ27/cytochrome oxidase I, II (SEQ ID NO:7)
GCCACGAAGGCGTAAAACCGACCCCATGACCCCTAACAGGGCCCTCTCAGCCCTC

CTAATGACCTCCGGCCTAGCCATGTGATITCACTTNCACTCCATAACGCTCCTCAT

ACTAGGCTACTAACCAACACACTAACCATATACCAATGATGGCCGCATGTAACAC

G

SZ38/L6/TAXREB107, 140 (SEQ ID NO:8)
GCCACGAAGGCCCGCAACCCTGTCCTTGTCAGAGGAATTGGCAGGTATTCCCGAT

CTGCCATGTATCCAGAAAGGCCATGTACAAGAGGAAGTACTCAGCCGCTAAATCC

AAGGTGAAAAGAAAAAGAAGGAGAAGGTTCTCGCAACTGTTACAAAACCAGTTG

GTGGTGACAAGAACTGGCACTGGATCCCGTGTGGTTAACTTCGCAAA

SZ12/S7 (SEQ ID NO:9)
GCCACGAAGGCAGAAAATCCAAGTCCGGCTAGTACGCGAATTGGAGAAAAAGTT

CAGTGGGAAGCATGTCGTCTTTATCGCTCAGAGGAGAATTCTGCCTAAGCCAACT

TABLE 2-continued

CGAAAAAGCCGTACAAAAAATAAGCAAAAGCGTCCAGGAGCCGTACCTGACAGC

TGTGCACGA

SZ34/ERCC3/XP-B (SEQ ID NO:10)
GCCACGAAGGCGAATATGCCATTCGACTGAACAAACCCTATATCTACGGACCT

ACGTGTCAGGGGGAAAGGATGCAAATTCTCCAGAATTTCAAGCACAACCCCAAA

ATTAACACCATCTTCATATCCAAGGTAGGTGACACTTCGTTTGATCTGCCGGAAG

CAAATTGTCTCATTCAGATCTCATCCCATGGTGGCTCCAGGCGTCAGGAAGCCAA

UNKNOWN SEQUENCES
SZ29 (SEQ ID NO:11)
CACTACAATGGATGATGTATATAACTATCTATTCGATGATGAAAGATACCCCACC

AAACCCAAAAAAAGAGATCTGGAATTCGGATCCTCGAGGCCACGAAGGCCGGAA

ATCTGAAGCAAAGAAGGAATCACTTCCCAGAAGAAGAAGCCTGCATATCGAACC

TTTATTAAAGGAAAAAATTACATGAAGCAACGGGATGACATTTTGATTAACAGGC

CNGCAAAGAANCACCTANAATTGTATGACAGGGATCTGAAACATTTTCGGATCTC

TAAGGCNCTCGATANANTTCTTGATCCCACTTGTNCAATAAAGCACCCGAGATT

NCGGTGTCCATCATAAAGGAGTTNAATCGAAGAAGAGTCCTTGCAAATGCGCTTG

CANGTCTGGATGAAAAAGAAATCANTCNTGTTCTTAATTTTTTGATAANGAATCT

NTCTCCCCNAGATTTGCCCCTGTTTTAATCNNTGCTGCTGAAATAATTATTGATAT

ATATCTGCCTGTNATTGGTCCTCCCCTGTANTTGATAAAAAGTTTTTACTACTTCN

NGGACTTGTTTAAAAAGANATTGATTNCCCAGANAATTGTTNIAAACCTTGGGGGA

TGATNGATATGCTNTTGCCCCNTGAAAAAGAAGGAAGGCCNTCTTTNTTTGNACA

CCCCTCTGATGGATTCCCCAAAATAANAAAATAAATCCTNNTGTCTGCTAATAAA

ACTNTAAAACTCCNAAATTTGAATAAATTTGACTGTTTTNATTTTTGGGAAAAAA

NCNCTTTGATACTTTTAAAAACTGTTTGCNAAACCCTTCTNTGGAAAAAACGGAA

TAATTTTGGCCGGAAACCATTTCCTTTTAANTTTAAAATGGTTTCCCCTTTTNTTT

TGAATTTTACCCCTCCCCNNAAAATTTCCNTTTTTTTTCCCCAATTTGTTTTCNTGG

GATGGAATTTANTTTTATACCGGATTTTTTTTTTCCCCNTTTGGTTTGTTTTCCATT

GGGAATCCATTTAAACCCCCCNGGAAAAGGTCCCTNGGAACCN

Z2/unknown (SEQ ID NO:12)
GCCACGAAGGCGTTTCACGTCTTCGCCAATACAGTGAGCAAGGCAATTCTCT

CAGAAACCCCCACGTGTGCACAGTGGGAGAGGGGAAAGAGAAAAAAAGGTGAG

CATGQAGGAAAAAGGTACTGGATAAAGTAAACTTCAAACCTTAGGGC

SZ33 (SEQ ID NO;13)
GNNNNNNNNTTNCTCNCTACAATGGATGATGTATATAACTACCTATTCGATGAT

GAAGATACCCACCAAACCCAAAAAAAGAGATCTGGAATTCGGATCCTCGAGGCC

ACGAANGCCGGCCTTCGTGGCCGAAAAGAGCTGAGCGGAGACCAAAGTCAGCCG

GGAGACAGTGGGTCTGTGAGAGACCGAATAGAGGGGCTGGGGCCACGAGCGCCA

TTGACAAGCAATGGGGAAGAAACAGAAAAACAAGAGCGAAGACAGCACCAAGG

ATGACATTGATCTTGATGCCTTGGCTGCAGAAATAGAANGAGCTGGTGCTGCCAA

AGAACAGGAGCCTCNAAAGTCNAAAGGGAANAAGAANAAAGAGAANANNAAGC

AGGACTTTGATGAAGATGATATCCTGAAAGAACTGGAAGAATTGTCTTTGGAAGC

TCAAGGCATCNAAGCTGACAGANAAACTGTTGCAGTGAAGCCNACAGAAAACAA

TABLE 2-continued

```
TGAAGAAGAATTCCCCTCCNAGATNNNNNNNAGAAAGGACCGAAGGGCNAAAA

ACAGAATTTTGATGATAATGATACGAAGAATTGGAAGATAAAGATTCCNAATCC

ANAAAGACTGCNAAACCGAAAGTGGAAATTTCTCTGGGANTGATGATGATGATG

ATTTTAACCAACTTCCTAAAAAATNAAGGGAAAGCTCCNAAATCAATAANAAA

TTGGATGGTCCAAGAAGATGAGGATACCTTNNNAATTTANGANCTTCANAATAAT

TCTCTGGTGAAATTGTGATAATCCATAATTTTGCNTCTTNAAANGGCGAAAAAN

TCNAAAACCNCCCGTTCTNCCTTNAANTTGGATGAAAATATACCCNCCTCCAATT

AAACNTGGCCCNAANAAGGCAANNNAGGACNCAANAAAAAACCAAATAAAAAA

ACNAACNCGGAACTGAANAAAAAAAATTTAAACCGTTTNGGTTTAATTTCCNN

GGTTNCCCGGGANTTNAAAAAAAANTTGCCTCCTGCCCCAAATTNTTAANCN
```

SZ37 (SEQ ID NO:14)
```
GNNNNGNNTTCNNCCACTACAATGGGATGATGTATATAACTACCTATTCGATGAT

GAAGATACCCACCACACCCNAAAAAAAGAANNTCTNGGATTCCGGNTCCTCGAG

GCCACGAAAGGCCGGCCTTCGTGGCCGAAAAGAGCTGAGCGGAGACCAAAGTCN

GCCGGGAGACAGTGGGTCTGTGAGAGACCGAATAGAGGGGCTGGGGCCACGAGC

GCCATTGACAAGCAATGGGAAGAAACAGAAAAACAAGAGCGAAGACAGCACC

AAGGATGACATTGATCTTGATGCCTTGGCTGCANAAATAGAAAGAGCTGGTGCTG

CCNAAGAACAGGAGCCTCNNAAGTCTCNAGGGAAANAGAAAANAGAGAATANN

NAGCCCGACTTTGATGAAGATGATATCCTGAAAGAACTGGAAGAATTGTCTTTGG

AACTCNNGGCATCTAAGCTGACAGANAAACTGTTGCNNTGAAGCCCCCANAAAA

CNATGAAGAAGAATCCCCTCCCNAGATTNNNNANAGAAAGGACANANGGGCCN

NAACAGANTTTTGATGATAAGATAGCGAANAATTGGAAGATATAGATTCNCAA

TCNCNNNAGACTGCCCANCCNAAAGTGGAAATTTNTCTNGGAGTGATGATGATG

ATGATTTAACANACTTCCTCNAAAANCTNNAGGGAAAGCTCCAAATCNNATAAN

AAATNNGATGGGTCTCAAGAAGATNAGGATACNTTTNNNATTTTNAACGTCCCNA

ATAAATTCCTCTNGTGAAATTGTGATAATCCATAATTTTTGCCTCTCCAAAAGGAC

CAAAAAAATCCAAAANCCNCCCCNTCCCCCTTNAAATTNGATTANAATTTACCCN

CCTCCCATTTAAACCTGNCCCNNAAGGCGAAAAAAAGGGCNCCNANNAAAANNCC

CANTAATAANAACCNACCGCGGGGCTTANNAAANAAAAATTTAACCGTTTTNGG

TTNATTTCCNCNGGACCCCCNGGATTTTAAAAAACTTTGCCTCCTGGCCCCAAATT

TTTAATCTAA
```

---

What is claimed is:

1. A method for modulating cell division regulation comprising the introduction to a cell in vitro at least one agent for binding with mdm2 in the cell, wherein the agent is a polypeptide encoded by a nucleic acid selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14, or a fragment of the polypeptide thereof that binds mdm2.

2. A composition for use in modulating apoptosis through interaction with mdm2 comprising a suitable carrier dilutant or excipient and at least one agent, wherein the agent is a polypeptide encoded by a nucleic acid selected from the group consisting of SEQ ID NO: 1, SEQ ID NO: 2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14, or a fragment of the polypeptide thereof that binds mdm2.

3. A method of using a polypeptide encoded by SEQ ID NO: 3 in the manufacture of a composition for use in modulating apoptosis through interaction with mdm2, comprising combining the polypeptide with a suitable carrier dilutant or excipient.

4. A diagnostic/prognostic assay kit for determining cell division regulation comprising a means for determining cellular levels of a polypeptide and/or a means for detecting the polypeptide, wherein the polypeptide is encoded by a nucleic acid selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO: 9, SEQ ID NO:10, SEQ ID NO:11, SEQ ID NO: 12, SEQ ID NO: 13, and SEQ ID NO: 14, or a fragment of the polypeptide thereof that binds mdm2.

5. A diagnostic/prognostic assay kit according to claim 4 wherein said assay is an immuno assay.

6. A method for treating aberrant cell division so as to arrest, mitigate or reverse said aberrant cell division wherein said method comprises administering to a cell in vitro to be treated an effective amount of at least one agent, wherein the agent is a polypeptide encoded by a nucleic acid selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14, or a fragment of the polypeptide thereof that binds mdm2.

* * * * *